United States Patent [19]

Cunliffe et al.

[11] 4,448,714
[45] May 15, 1984

[54] ANTIBIOTIC POLYPEPTIDE COMPOUNDS PREPARED FROM STAPHLOCOCCUS BACTERIA

[76] Inventors: William J. Cunliffe, 47 Tredgold Ave., Bramhope, Nr. Leeds; Elizabeth A. Eady, 20 Woodlea Rd.; Keith T. Holland, 13 Hall Park Ave., Horsforth, both of Leeds, all of England

[21] Appl. No.: 270,523
[22] PCT Filed: Oct. 13, 1980
[86] PCT No.: PCT/GB80/00164
   § 371 Date: Jun. 4, 1981
   § 102(e) Date: Jun. 4, 1981
[87] PCT Pub. No.: WO81/00962
   PCT Pub. Date: Apr. 16, 1981

[30] Foreign Application Priority Data

Oct. 12, 1979 [GB] United Kingdom ............... 79/35534

[51] Int. Cl.$^3$ .............................................. C07G 7/00
[52] U.S. Cl. ................................. 260/112 R; 435/68; 435/884; 424/177
[58] Field of Search ................. 424/177, 116; 435/68, 435/884; 260/112 R

[56] References Cited

U.S. PATENT DOCUMENTS

3,278,378 10/1966 Schindler ............................. 435/68
3,764,670 10/1973 Katzirkatchalsky ............... 424/118
4,147,774 4/1979 Umezawa ........................... 424/118

FOREIGN PATENT DOCUMENTS

1080050 12/1954 France.
2805813 8/1979 Fed. Rep. of Germany.

OTHER PUBLICATIONS

Selwyn, P. D. et al., Chemotherapy-Proc. 9th Int. Cong. Chemotherapy, vol. 5, pp. 391–396, 1975.
Pulverer, G. et al., Pro. III Int. Symp. Staph and Staph Infec., pp. 599–621, 1976.
Loeb, L. J. Can. J. Res. 28E, pp. 212–216, 1950.
Hsu, C. et al. Can. J. Microbiol., vol. 17, pp. 1223–1226, 1971.
Holland, K. T. et al., J. Med. Microbiol., vol. 12, pp. 71–82, 1979.
Halbert, S. P. et al., J. Immunol., vol. 70, pp. 400–410, 1953.
Hsu, C. et al., Can. J. Microbiol., vol. 18, pp. 121–125, 1972.
Su, T. L., J. Exp. Pathol., vol. 29, pp. 473–481, 1948.
Chem. Abs. 77:16130f 1972.
Chem. Abs. 82:71597d 1975.
Karzybski et al., Antibiotics; Origin, Nature and Properties, Vol. 1, Polish Scientific Publishers (1967) Pages 31–32.

*Primary Examiner*—John C. Bleutge
*Assistant Examiner*—Patricia Short
*Attorney, Agent, or Firm*—Hammond & Littell, Weissenberger & Dippert

[57] ABSTRACT

The invention relates to an antibiotic polypeptide compound, or addition salt thereof, having a molecular weight no greater than 10000 and possessing bactericidal and bacteriolytic activities in respect of Gram-positive bacteria, the said compound comprising within the molecular structure thereof amino acid derivative units of formulae

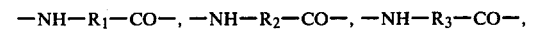
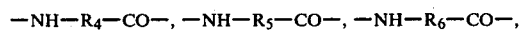
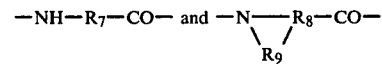

wherein $NH_2-R_1-COOH$, $NH_2-R_2-COOH$, $NH_2-R_3-COOH$, $NH_2-R_4-COOH$, $NH_2-R_5-COOH$, $NH_2-R_6-COOH$ and $NH_2-R_7-COOH$ respectively represent isoleucine, phenylalanine, alanine, aspartic acid, glutamic acid, lysine and glycine and

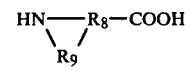

represents proline The invention further provides a process for the preparation of antibiotic polypeptides by the aerobic culturing of a strain of *S. epidermidis*.

The invention also provides compositions comprising antibiotic substances and methods of treatment therewith.

The invention further provides a new strain of *Staphylococcus epidermidis* which produces the antibiotic polypeptides, compositions containing the said strain and a method of cosmetic or prophylactic treatment of the human skin with such compositions.

4 Claims, 5 Drawing Figures

ANTIBIOTIC POLYPEPTIDE COMPOUNDS PREPARED FROM STAPHLOCOCCUS BACTERIA

This invention relates to antibiotic substances, a process for the preparation and compositions thereof and methods of treatment therewith. The invention further relates to a new strain of *Staphylococcus epidermidis* which produces the antibiotic substances, compositions, containing the said strain and a method of cosmetic or prophylactic treatment of the human skin with such composition. The antibiotic substances having a bactericidal action against Gram-positive bacteria.

Staphylococci are known to produce at least three classes of substances having an inhibitory action on the growth of bacteria, namely bacteriocins, bacteriolytic enzymes and low molecular weight antibiotics. Publications describing the production of low molecular weight antibiotics from staphylococci are as follows:

HSU, C-Y. and WISEMAN, G. M., Can. J. Microbiol, 17 (1971), p 1223-1226.

LOEB, L. J., MOYER A. and MURRAY, R. G. E., Can. J. Res., 28E (1950), p 212-216.

PULVERER, G. and JELJASZEWICZ, J. Proceedings of III International Symposium on staphylococci and staphylococcal infections, p 599-621. Edited by J. Jeljaszewicz. Stuttgart: Fischer-Verlag.

SELWIN, S., MARSH, P. D. and SETHNA, T. N., Chemotherapy. Proceedings of the 9th International Congress of Chemotherapy, 5 (1975), p 391-396. Edited by J. D. Williams and A. M. Geddes. New York.

SU, T. L., Br. J. Exp. Pathol., 29 (1948), p 473-481.

HALBERT, S. P., SWICK, L. and SONN, C., J. Immunol., 70 (1953) p 400-410.

None of the low molecular weight antibiotics described in the above-mentioned publications has however been demonstrated to exhibit a bactericidal action resulting in lysis of the bacterial cells.

In J. Med. Microbiol, 12 (1979), p71-82, experiments are described in which numerous strains of resident human skin bacteria comprising 93 isolates of *Propionobacterium acnes* and 148 isolates of Micrococcaceae were screened for their ability to inhibit the growth of various indicator strains of *P. acnes* and *Staphylococcus epidermidis*. Fifty-three strains out of those tested showed some activity against at least one indicator strain, and both broad- and narrow- spectrum inhibition was detected. The strains which were examined were derived from 36 acne patients and 8 control subjects, and the main purpose of the investigations was to find whether the possession of inhibiting strains and conversely the possession of sensitive strains in patients results in a predisposition to acne. The particular strains of *P. acnes* and Micrococcaceae which were screened are not identified except by means of an internal reference. Moreover there is no description of any attempt to recover the active substances responsible for the inhibition which was observed.

The present invention is based upon the discovery that a particular strain of *Staphylococcus epidermidis*, i.e. Staphylococcus epidermidis NCIB 11536 (which was deposited in the National Collection of Industrial Bacteria, Torrey Research Station, P.O. Box 31, 135 Abbey Road, Aberdeen AB9 8DG 3rd October, 1979), or a mutant strain thereof, can be cultured to produce a new low molecular weight antibiotic polypeptide which exhibits broad spectrum activity against Gram-positive bacteria and which is distinguished from the low molecular weight antibiotics hitherto produced by staphylococci by the fact that it possesses a bactericidal action resulting in lysis of the bacterial cells.

According to one aspect of the present invention we therefore provide an antibiotic polypeptide compound, or addition salt thereof, having a molecular weight no greater than 10000 and possessing bactericidal and bacteriolytic activities in respect of Gram-positive bacteria, the said compound comprising within the molecular structure thereof amino acid derivative units of formulae

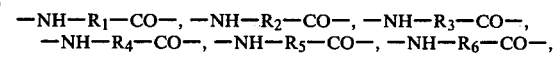
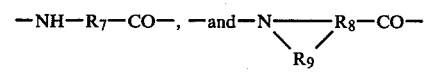

wherein $NH_2$—$R_1$—COOH, $NH_2$—$R_2$—COOH, $NH_2$—$R_3$—COOH, $NH_2$—$R_4$—COOH, $NH_2$—$R_5$—COOH, $NH_2$—$R_6$—COOH and $NH_2$—$R_7$—COOH respectively represent isoleucine, phenylalanine, alanine, aspartic acid, glutamic acid, lysine and glycine and

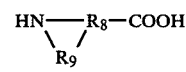

represents proline. The compound has UV absorption maxima at about 210 nm and at from about 260 to 280 nm.

Particularly suitable amongst the antibiotic polypeptides of the present invention is an antibiotic molecular weight of about 950 and comprising within the molecular structure thereof an amino acid derivative unit of each of the following formulae

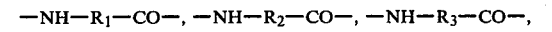
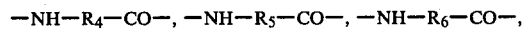
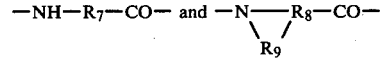

and a further amino acid derivative unit of formula

—NH—$R_7$—CO— wherein
$NH_2$—$R_1$—COOH, $NH_2$—$R_2$—COOH, $NH_2$—$R_3$—COOH, $NH_2$—$R_4$—COOH, $NH_2$—$R_5$—COOH, $NH_2$—$R_7$—COOH and

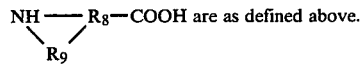

are as defined above.

It should of course be realized that antibiotic polypeptides may retain their antibiotic properties when the amino acid sequence or content of the polypeptide is altered. Antibiotic polypeptides and addition salts thereof as defined above are therefore deemed to fall within the scope of the present invention when one or more, suitably from 1 to 3, of the said amino acid derivative formula units, with the exception of those units of formulae —NH—$R_1$—CO— and —NH—$R_2$—CO— (wherein $NH_2$ $R_1$ COOH and $NH_2$ $R_2$ COOH are as defined above), are absent or replaced by formula units derived from different amino acids.

According to a further aspect of the present invention we provide a process for the preparation of an antibiotic compound possessing bactericidal and bacteriolytic activities in respect of Gram-positive bacteria, which both ingredients being as marketed by Oxoid Limited of Southwark Bridge Road, London SE1 9HF, England.

(iv) Synthetic Medium

This is a medium as described by Griffith, C. J. and Melville, T. H., Arch. Oral. Biol., 19 (1974), p 87–90, having the following composition:

| Component | Concentration mg liter$^{-1}$ | Component | Concentration mg liter$^{-1}$ | |
|---|---|---|---|---|
| K$_2$HPO$_4$ | 1,750 | Biotin | 0.006 | |
| KH$_2$PO$_4$ | 1,750 | Nicotinic acid | 2.3 | |
| Trisodium citrate | 500 | Thiamin | 1.0 | |
|  |  | Pyridoxine HCl | 12.0 | |
| PIPES (Piperazine-N—N$^1$—bis(2-ethane sulphonic acid)) | 5,000 | Calcium pantothenate | 1.2 | |
|  |  | Glucose | 0.2% | (w/v) |
| L-alanine | 100 |  |  | |
| L-arginine | 200 | Salts solution: |  | |
| L-asparagine | 100 | MgSO$_4$.7H$_2$O | 200 | |
| L-aspartic acid | 200 | Fe citrate | 10 | |
| L-cysteine | 100 | MnSO$_4$.4H$_2$O | 10 | |
| L-glutamic acid | 500 | NaCl | 10 | |
| Glycine | 100 | CaCl$_2$ | 10 | 5 ml. l$^{-1}$ |
| L-histidine | 100 | ZnCl$_2$ | 5 | |
| L-hydroxyproline | 100 | CuSO$_4$ | 0.5 | |
| L-isoleucine | 100 | CoNO$_3$ | 5 | |
| L-leucine | 100 |  |  | |
| L-lysine | 100 |  |  | |
| L-methionine | 100 | Agar | 1.0% | (w/v) |
| L-phenylalanine | 100 |  |  | |
| L-proline | 100 |  |  | |
| L-serine | 200 |  |  | |
| L-threonine | 200 |  |  | |
| L-tryptophan | 100 |  |  | |
| L-tyrosine | 100 |  |  | |
| L-valine | 100 |  |  | |
| Adenine | 10 |  |  | |
| Guanine | 10 |  |  | |
| Uracil | 10 |  |  | | process comprises the steps of aerobically culturing *Staphylococcus epidermidis* NCIB 11536 or a mutant strain thereof in or on a culture medium therefor and thereafter recovering the said antibiotic compound.

As an alternative to the process of the present invention it may prove possible to manufacture the antibiotic polypeptides of the present invention by non-microbiological processes comprising the step-by-step building up of the polypeptide chain by a succession of individual peptide condensations.

The process according to this invention can be carried out using a fluid or solid culture medium which contains carbon and nitrogen sources together with appropriate inorganic salts and other nutrients. Suitable culture media are provided for example by the following:

(i) Brain Heart Infusion Agar (BHIA)

This is a commercial medium marketed by Difco Laboratories of Central Avenue, West Molesey, Surrey, England and contains infusions from calf brains and beef hearts, proteose peptone (Difco), bacto-dextrose, sodium chloride and disodium phosphate (ii) Trypticase Soy Broth This is a commercial medium marketed by Becton Dickinson & Co. Limited of Empire Way, Wembley, Middlesex, England and containing pancreatic digest of casein, papaic digest of soybean meal, sodium chloride and disodium phosphate.

(iii) Tryptone L42/Yeast Extract L21 Medium

This is a medium made up to contain 2% by weight of Tryptone L 42 and 1% by weight of Yeast Extract L 21, The culture step is carried out aerobically, conveniently at a temperature of 35° to 40° C., preferably about 37° C., for about 12 to 48 hours, preferably 24 to 36 hours. The initial pH of the culture medium is conveniently in the range of from 4.5 to 7, pHs of from 5 to 6.5 being preferred.

After completion of the culture step, the new antibiotic substance is recovered from the culture medium. Methods which have been found to be useful in carrying out the recovery step are as follows:

1. Freeze-thaw extraction

This is a well-known technique as described for example by McGeachie J., Zentrabl. Bakteriol. (Orig A), 196 (1965), p 377–384. The extracted fluid can then be centrifuged to remove the bacteria. The crude freeze-thaw extract thus obtained, if desired for use in the assay of the antibiotic, can be sterilised by filtration through a cellulose acetate membrane filter (pore diameter, 0.45 μm, Oxoid Ltd.) and stored at 4° C. until required. Non-sterile extract can be stored at −20° C.

2. Evaporation

The pH of crude freeze-thaw extracts is made acid, preferably to about pH5 and conveniently by the addition of 10 N HCl, before evaporation because the inhibitory activity of the new antibiotic substance is only heat stable under acidic conditions. Evaporation can conveniently be carried out at 90° C. on a rotary evaporator (Rotavapor-EL, Buchi, Switzerland) under reduced pressure.

3. Ultrafiltration

Concentration or dialysis can be achieved by positive pressure filtration using the appropriate filtration membrane, e.g. in an Amicon model 52 (capacity 65 ml) as marketed by Amicon Limited, High Wycombe, Buckinghamshire, England. Five double volume changes of distilled water are conveniently used for dialysis.

4. Ammonium sulphate precipitation

Ammonium sulphate is added to the freeze-thaw extract to obtain 25 to 30% saturation. After stirring, the protein thereby precipitated can be removed, e.g. by centrifugation. The supernatant is then brought to 50-60% saturation by the addition of further $(NH_4)_2SO_4$ again followed by stirring and centrifugation. The precipitate, which contains the antibiotic substance, can then be resuspended in a minimum volume of buffer, e.g. 0.05 M phosphate buffer, pH 6.0. In carrying out this purification step, $(NH_4)_2SO_4$ is preferably first added to obtain about 30% saturation and subsequently added to obtain about 50% saturation.

5. Ion-exchange chromatography

A sample partially purified by evaporation or ammonium sulphate precipitation is loaded on to a Sephadex C-25 cation-exchange column. Unbound substances are eluted with starting buffer, e.g. 0.05 M phosphate buffer, pH 6.0. Bound substances can then be eluted at a flow rate of 15 ml $h^{-1}$ using a linearly increasing ionic strength gradient of 0-0.5 M (400 ml) NaCl in 0.5 M phosphate buffer, pH 6.0 and 5.5 ml fractions are collected.

6. Gel filtration chromatography

A sample partially purified by evaporation, ammonium sulphate precipitation and/or ion exchange chromatography is loaded on to a Sephadex G-50 column and eluted, e.g. with 0.05 M phosphate buffer, pH 6.0. If desired, Sephadex G-25, Sephadex G-15 or Biogel P2 columns can be used instead of the Sephadex G-50 column.

In the ion exchange and gel filtration steps above it has been found that the eluted antibiotic polypeptide of the present invention frequently has a significant NaCl content. This arises from the highly cationic nature of and the aromatic residue within the polypeptide causing it to bind strongly to gel filtration media (whether polyacrylamide or dextran gels) and so requiring the use of high ionic strength buffers for its release.

In practice therefore three alternative combinations of ion exchange and gel filtration chromatography steps have been developed for operation on samples partially purified by evaporation or ammonium sulphate precipitation:

(a) to yield a high titre containing NaCl by elution through a Biogel P2 or Sephadex C15 column followed by elution through a Sephadex C25 column;

(b) to yield a lower titre of low NaCl content by elution through a Sephadex C25 column followed by elution through a Sephadex G10 column; and (c) to combine removal of high molecular weight material with removal of NaCl by elution through a Sephadex G15 column followed by elution through a Sephadex C25 column followed by elution through a Sephadex G10 column.

It will be appreciated that the purification steps as described above are by way of example, and that these steps can be modified or replaced by other purification steps as desired. For example, it may be possible to replace the ammonium sulphate precipitation step by a similar step using other precipitating agents such as ethanol or acetone.

Preferably, the recovery step involves freeze-thaw extraction, ammonium sulphate precipitation, ion-exchange chromatography and gel filtration chromatography.

As an alternative to freeze-thaw extraction, a further preferred recovery step involves centrifuging the incubated medium at about 3000 g for about 30 minutes to remove cell material and then subjecting the supernatant fluid to the ammonium sulphate precipitation and subsequent steps as described for the freeze-thaw extract. This is particularly suitable when incubation has been effected in Brain Heart Infusion Broth.

It has been established that in the ion-exchange chromatography or gel filtration chromatography step, there is a separation of two antibiotic substances. Thus, for example, upon ammonium sulphate precipitation followed by gel filtration chromatography as hereinbefore described, two peaks of inhibitory activity against selected indicator strains of *S. epidermidis* (code number MF 87) and *S. cohnii* (code number MF 121) were detected. A quantitative determination of inhibitory activity is effected by a modification of the method of Dajani and Wannamaker, J. Bacteriol, 97 (1969), p 985-991. Serial 2-fold dilutions of the preparation of antibiotic substances were made in either Brain Heart Infusion (crude preparations obtained by freeze-thaw extraction) or 0.05 M phosphate buffer, pH 6.0 (column fractions) using 0.5 ml volumes. A 0.02 ml volume of each dilution was spotted on to the surface of a seeded plate of each indicator organism and allowed to dry. Plates were incubated aerobically for 6-7 h at 37° C. The dilution producing a definite reduction in the density of growth of the indicator strain was regarded as the end point and was considered to contain 1 unit of inhibitory activity $ml^{-1}$. FIG. 1 of the accompanying drawings illustrates the results obtained on column fractions obtained by gel filtration chromatography and it will be noted that there is a minor peak which eluted in the void volume and a major peak which was retained by the gel. The results illustrated in FIG. 1 are of ammonium sulphate precipitated inhibitor eluted through Sephadex G50 using a 0.05 M phosphate buffer at pH 6.0. The total recovery of activity from the column was 84.3%. It has been established that the minor peak is provided by a substance of relatively high molecular weight (possibly greater than 30,000) and that the major peak is provided by a substance of relatively low molecular weight (less than 10000). There was a 20 fold increase in the specific activity of the low molecular weight antibiotic substance, the antibiotic polypeptide, (from 2.06 to 40 units $mg^{-1}$ protein against MF121) but not of the larger molecular weight antibiotic substance as shown by the following Table 1:

TABLE 1

| Fraction | Total units of activity against MF121 | Total protein mg. | Specific activity units $mg^{-1}$ protein | Overall Yield, % |
|---|---|---|---|---|
| Crude freeze-thaw extract | 5120 | 2480 | 2.06 | |
| Ammonium sulphate precipitate | 1280 | 96 | 13.3 | 25.0 |
| Relatively high molecular weight antibiotic substance (pooled) | 45 | 46 | 0.98 | 0.88 |
| Relatively low molecular weight antibiotic | 1040 | 26 | 40 | 20.3 |

TABLE 1-continued

| Fraction | Total units of activity against MF121 | Total protein mg. | Specific activity units mg$^{-1}$ protein | Overall Yield, % |
|---|---|---|---|---|
| substance (pooled) | | | | |

Fractions of the high molecular weight antibiotic substance did not inhibit the indicator strain *S. epidermidis* (MF 87) until reconcentrated by ultrafiltration. They represented only 4.0% of the activity recovered from the column. It is the antibiotic substance of relatively low molecular weight, responsible for the major peak in FIG. 1, which is the antibiotic substance of principal interest in the present invention.

The mode of action of the low molecular weight antibiotic substance according to the invention against *S. epidermidis* (MF87) has been studied in growth medium (BHI) and non-growth medium (phosphate buffer) to determine whether this mode of action is bacteriostatic, bactericidal or bacteriolytic. For the determination of the mode of action, *Staphylococcus epidermis* (MF 87) was grown overnight at 37° C. and used as the substrate at an initial concentration of $10^8$ cells ml$^{-1}$ BHI or 0.5 M phosphate buffer, pH 6.0. Inactive inhibitor was used as a control and was obtained by autoclaving at 121° C. for 0.25 h at pH 9.0. The pH was readjusted to 6.0 before use. Active substance was obtained either by Sephadex G50 chromatography of an evaporated concentrate (for studies in growth medium) or by ion-exchange chromatography of the low molecular weight substance on Sephadex C-25 (for studies in non-growth medium). Equal volumes of cells and antibiotic substance (or autoclaved antibiotic substance) were mixed at $T_o$ and portions of each mixture were incubated at 37° C. in cuvettes held in an automated double beam spectrophotometer (SP1800, Pye Unicam) set at 600 nm reading at 0.08 h intervals. The remainder of each mixture (also incubated at 37° C.) was used to obtain viability count readings. The microscopic appearance of the bacteria was determined hourly by Gram staining.

FIG. 2 of the accompanying drawings shows the changes in viability count and optical density of a suspension of cells of *S. epidermidis* (MF 87), in growth medium, in the presence and absence of the antibiotic. In the absence of the antibiotic the organisms grew and reached the stationary phase after 5.25 h incubation. However, in the presence of the antibiotic the viability count began to fall immediately and was reduced to 10% of its initial level after 0.17 h, with no reduction in optical density. Shortly afterwards the optical density began to fall and after 6 h incubation had almost reached zero. At this point the viability count was 10 organisms ml$^{-1}$. Gram-stained films of the control culture at all times revealed intact Gram-positive cocci. The culture containing the antibiotic started to lyse after 0.17 h (Gram-negative cells, morphology indistinct, Gram-negative material outside cells) and the extent of lysis increased with prolonged incubation. After 4 h incubation few intact cells remained.

In non-growth medium similar results were obtained although the effect of the inhibitor was reduced so that the viability count fell to 10% of its initial level after 0.5 h (compared with 0.17 h in growth medium).

The following properties of the antibiotic substances (both low and high molecular weight) produced in the culture process according to the present invention, and the crude preparations from which they are recovered, have been observed.

1. Protease sensitivity (of the low molecular weight antibiotic substance)

The ion-exchanged low-molecular weight antibiotic substance (containing 1.75 mg ml$^{-1}$ protein) was sensitive to trypsin (2.5 mg ml$^{-1}$) but resistant to thermolysin (160 μg ml$^{-1}$), subtilisin (650 μg ml$^{-1}$) and pronase (1.5 mg ml$^{-1}$). Activity was measured at pH 6.0 in 0.05 M phosphate buffer. Incubation was at 37° C. for 3 h.

2. Inhibition spectra of the crude preparation (i.e. freeze-thaw extract) and of the separated low and high molecular weight antibiotic substances.

Table 2 below shows the inhibition spectra of the crude freeze-thaw extract, the low molecular weight antibiotic substance and the high molecular weight antibiotic substance. These were separated by gel filtration of an ammonium sulphate precipitate on Sephadex G50.

TABLE 2

Activity spectra of various inhibitor preparations

| Organism | Test medium | Susceptibility to Low mol. wt. antibiotic substance | High mol. wt. antibiotic substance | Crude preparation (Freeze-thaw extract) |
|---|---|---|---|---|
| S. aureus (3 strains) | 6BHIA | + | − | + |
| S. epidermidis | " | + | ± | + |
| S. cohnii (MF121) | " | + | + | + |
| M. luteus | 6BHIA | + | + | + |
| M. roseus | " | + | + | + |
| P. acnes | 6BHIA | ± | ND | ± |
| P. avidum | " | + | ND | + |
| P. granulosum | " | ± | ND | ± |
| S. pyogenes | 6BHIA | + | − | + |
| S. faecalis | " | − | − | − |
| S. zymogenes | " | + | − | + |
| S. viridans | " | + | + | + |
| A. viridans | 6BHIA | + | + | + |
| B. cereus | 6BHIA | − | − | − |
| B. megaterium | " | + | + | + |
| B. laterosporus | " | − | − | ± |
| B. sphaericus | " | + | + | + |
| C. diphtheriae gravis | 6BHIA | + | − | + |
| C. xerosis | " | + | + | + |
| C. hofmannii | " | + | + | + |
| L. monocytogenes | 6BHIA | + | − | + |
| C. sporogenes | FBA | − | − | − |
| C. bifermentans | " | + | + | + |
| C. perfringens | " | + | − | + |
| Arthrobacter oxydans | 6BHIA | + | + | + |
| Cellulomonas subalbus | " | + | + | + |
| P. ovale | Peptone Ox Bile | − | − | − |
| N. meningitidis | HBA | − | − | − |
| N. gonorrhoeae | " | − | − | − |
| N. pharyngis | " | − | − | − |
| H. influenzae | HBA | − | − | − |
| Chromobacterium violaceum | 6BHIA | − | − | − |
| E. coli (2) | 6BHIA | − | − | − |
| P. vulgaris | " | − | − | − |
| P. morganii | " | − | − | − |
| S. typhimurium | " | − | − | − |
| K. aerogenes | " | − | − | − |
| K. pneumoniae | " | − | − | − |
| A. faecalis | " | − | − | − |

TABLE 2-continued

| | | Susceptibility to | | |
|---|---|---|---|---|
| Organism | Test medium | Low mol. wt. antibiotic substance | High mol. wt. antibiotic substance | Crude preparation (Freeze-thaw extract) |
| *S. marcescens* | " | — | — | — |

Activity spectra of various inhibitor preparations

HBA = heated blood agar
FBA = fresh blood agar
6BHIA = Brain Heart Infusion Agar, pH 6.0
+ = zone of total inhibition in region of drop
± = zone of partial inhibition (reduced growth) in region of drop
− = no inihibition
ND = not done Activity was confined to inhibition of Gram-positive organisms. The spectrum of the low molecular weight antibiotic substance was identical to that of the crude preparation. Fewer organisms were inhibited by the high molecular weight antibiotic substance but this is thought to reflect its lower titre rather than a real difference in spectrum since those organisms which are not inhibited were those which showed greatest resistance to the crude preparation.

3. Other properties of the crude preparation (i.e. freeze-thaw extract)

The effects of various treatments on the activity of crude freeze-thaw extracts of the antibiotic(s) are shown in the following Table 3.

TABLE 3

The effects of various treatments on the activity of crude freeze-thaw extract

| TREATMENT | Initial* Titre | Final* Titre | % Remaining |
|---|---|---|---|
| 1. Heat: | | | |
| 37° C./16 h | 8 | 8 | 100 |
| 100° C./4 h | 8 | 8 | 100 |
| 121° C./15 min/pH 5 | 6 | 6 | 100 |
| 121° C./15 min/pH 9 | 6 | 0 | 0 |
| 2. pH (2 weeks/4° C.) | | | |
| pH 2 | 8 | 8 | 100 |
| pH 7 | 8 | 6 | 75 |
| pH 11 | 8 | 0 | 0 |
| 3. Evaporation 90° C., reduced pressure | 800 | 640 | 80 |
| 4. Amicon dialysis (PM30)** | 8 | 2 | 25 |
| 5. Adsorption: $10^{11}$ cells of *S. epidermidis* ml $^{-1}$ inhibitor, 5 mins/37° C. | 12 | 3 | 25 |

*Titre is expressed as units ml$^{-1}$ against MF87 (except in the case of evaporation when the titre is total units against MF87).
**Retains molecules >30,000 mol. wt.

It has been found that the activity is extremely thermostable at acidic pHs so that concentrated preparations could be obtained by evaporation of the freeze-thaw extracts at pH 5.0. The inhibitory activity was stable at 4° C. if the pH was acidic and was adsorbed on to sensitive cells of *S. epidermidis* at 37° C. The activity was precipitated by ammonium sulphate (0–50% saturation). During its production on BHI agar, inhibitory activity passed through a dialysis membrane (retention limit 14,000 molecular weight) placed on the surface of the agar between the producer culture and the growth medium of the indicator strain. However, the activity of crude preparations could not be totally removed by dialysis against distilled water. Ultrafiltration membranes of cut-off 10,000 and 30,000 molecular weight retained from 18.75–25% of the inhibitory activity. At least 99% of molecules capable of passing through the membrane should be removed by this procedure. These results indicate the presence of low molecular weight and high molecular weight antibiotic substances.

4. Activity of antibiotic substances in respect of *S. Epidermidis* NCIB 11536

It has been found that the high molecular weight antibiotic substance exhibits strong bacteriolytic activity in respect of *S. Epidermidis* NCIB 11536 whereas no such activity is observed for the low molecular weight antibiotic substance.

5. Amino acid analysis of low molecular weight antibiotic substance.

Amino acid analysis shows the low molecular weight antibiotic substance to be a polypeptide derived from isoleucine, phenylalanine, alanine, aspartic acid, glutamic acid, lysine, glycine and proline. In particular an amino acid composition of one unit derived from each of isoleucine, phenylalanine, alanine, aspartic acid, glutamic acid, lysine and proline and two units derived from glycine has been shown. In those polypeptide antibiotics already known in the art, the presence of isoleucine and phenylalanine has not been demonstrated. Hsu, C-Y and Wiseman, G. M. in Can. J. Microbiol. 18 (1972) 121-5, however, have reported epidermidins in which are present alanine, aspartic acid, glutamic acid, glycine, lysine and proline although it should be noted that the mode of action of these epidermidins is bacteriostatic rather than bactericidal and bacteriolytic 6. Mode of action of the antibiotic substances The crude preparation (i.e., the freeze-thaw extract) exhibits a bactericidal action resulting in lysis of the cells. It has been observed that the lysis resulting from the exposure of *S. epidermidis* cells to the low molecular weight antibiotic substance was not a primary effect of adsorption of the antibiotic substance since over 90% of the cells has been killed before lysis began. The activity is also exhibited on non-growth media.

In view of its bactericidal action and its broad spectrum of activity against Gram-positive bacteria, the low molecular weight antibiotic substance according to the invention is potentially useful in the treatment of Gram-positive bacterial infections, especially such infections of the skin. The low molecular weight antibiotic substance is of particular interest as being potentially useful in the treatment of skin infections such as infected eczema, impetigo, boils, cellulitis and more especially acne, the activity of the substance against a large number of indicator strains of *P. acnes* having been demonstrated. It is believed that the low molecular weight antibiotic, being produced by an organism normally resident on the skin, is likely to possess greater stability and activity on the skin than antibiotics in current usage.

According to a yet further aspect of the present invention we provide an antibiotic polypeptide compound, or addition salt thereof, as described above for use in a method of treatment of the human or animal body to combat Gram-positive bacterial infections, in particular Gram-positive bacterial skin infections in humans such as acne impetigo or infected eczema.

According to a yet further aspect of the present invention we provide a pharmaceutical composition comprising as active ingredient an antibiotic compound according to the present invention together with a pharmaceutical carrier or excipient.

The compositions according to the invention may be presented, for example, in a form suitable for oral, parenteral, enteral or topical application. Preparations for topical application are preferred, and such preparations may for example be in the form of solutions, emulsions, gels, lotions, ointments, creams or powders. Conventional pharmaceutical carriers and excipients, as well as the usual methods of production, may be employed for the preparation of pharmaceutical preparations according to the invention.

According to a yet further aspect of the present invention we provide a method of treatment of the human or animal body to combat Gram-positive bacterial infections which method comprises the application to the said body of an antibiotic compound of the present invention.

A preferred embodiment of the method of treatment according to the present invention of the human or animal body comprises the treatment of human acne, impetigo or infected eczema by the topical application to the human skin of a pharmaceutical composition of the present invention in a form suitable for the said topical application.

The strain S. epidermidis NCIB 11536 was isolated from the facial skin of an adult human and was identified according to the scheme of Kloos, W. E. and Schleifer, K. H., J. Clin. Microbiol., 1 (1975), p 82-88. The known characteristics of this strain are as follows:

History
  Original description of colouring: grey-white, proteolytic (on chocolate agar)
  Date of isolation May 1976
  Source: Skin surface of face, male caucasian, healthy skin (no acne vulgaris or evidence of any other skin disease), age 25 years.
  Storage: In 40% (v/v) glycerol/phosphate buffered saline (PBS)
  Growth conditions: Fluid culture—Brain Heart Infusion, overnight incubation, 37° C. aerobic.
  Inoculum: 0.1 ml from glycerol/PBS stock culture.
  (Note: long term storage—freeze-dried cultures and cultures held in liquid nitrogen).

| Characteristics: Test | Reaction |
|---|---|
| Coagulase | − |
| Phosphatase | + |
| Nitrate reduction | + |
| Novobiocin sensitivity | sensitive to 5 μg disc |
| Acid, aerobically from: | |
| glucose | + |
| mannitol | − |
| trehalose | − |
| sucrose | + |
| lactose | + |
| xylose | − |
| arabinose | − |
| maltose | + |
| fructose | + |
| ribose | − |
| Protease | + |
| Lipase triolein | + (plate test only) |
| tributyrin | + (plate test only) |
| Hyaluronidase | − |
| Haemolysis (horse or human blood) | + (plate test only) |
| Production of acetoin | + |
| DNase | + |

Nutrition (aerobic growth)
 1. Vitamin requirements: nicotinic acid thiamine biotin (can be substituted by oleic acid)
 2. Amino acid requirements: not fully determined but will grow on synthetic medium containing 7 amino acids.
 3. Does not require guanine, uracil or adenine for growth.

| Antibiotic sensitivities | Amount of antibiotic/disc |
|---|---|
| Sensitive to: ampicillin | 10 μg |
| penicillin G | 1 unit |
| carbenicillin | 100 μg |
| tetracycline | 10 μg |
| clindamycin | 2 μg |
| gentamycin | 10 μg |
| erythromycin | 5 μg |
| chloramphenicol | 25 μg |
| furoxone | 50 μg |
| novobiocin | 5 μg |

According to a yet further aspect of the present invention we provide Staphylococcus epidermidis NCIB 11536 or a mutant strain thereof, conveniently in a sterile medium.

Experiments reported by Selwyn, S., March, P. D., and Sethna, T. N. in Proc. 9th Int. Cong. of Chemotherapy 5 (1975) 391-6 indicate that Staphylococcus bacteria may be transferred to healthy skin on which they may flourish.

According to a yet further aspect of the present invention we therefore provide a cosmetic or prophylactic composition comprising Staphylococcus epipermidis NCIB 11536 or a mutant strain thereof together with a sterile carrier or excipient.

The cosmetic or prophylactic compositions of the present invention will preferably be in forms suitable for topical application to the skin.

According to a yet still further aspect of the present invention we provide a method of cosmetic or prophylactic treatment of the human skin to avoid the outbreak of acne, impetigo or infected eczema thereon which method comprises the topical application to the human skin of a cosmetic or prophylactic composition according to the present invention or of a cosmetic or prophylactic composition which comprises an antibiotic compound according to the present invention together with a carrier or excipient.

The following Example illustrates the invention:

Microorganisms

The indicator strains S. epidermidis MF 87 and S. cohnii MF 121, like the antibiotic producing strain S. epidermidis NCIB 11536, were isolated from the facial skin of an adult human. The strains were maintained in 40% (v/v) glycerol/PBS using a modification of the method of Gore L. F. and Walsh P., J. Med. Lab. Technol., 21 (1964), p 244-246.

Culture

An isolate of the strain S. epidermidis NCIB 11536 (taken from a stock culture maintained in 40% (v/v) glycerol/PBS as described above) was incubated in Brain Heart Infusion (BHI) broth in an amount of 0.1 ml of isolate per 10 ml of broth, the incubation being effected aerobically overnight at 37° C. with use of an orbital shaker.

0.1 ml portions of the broth culture thus obtained were inoculated on to plates of Brain Heart Infusion Agar (BHIA), the culture medium being as marketed by Difco Laboratories and having the following composition per liter of medium:

| | |
|---|---|
| Calf Brains, Infusion from | 200 g |
| Beef Heart, Infusion from | 250 g |
| Proteose Peptone, Difco | 10 g |
| Bacto-Dextrose | 2 g |
| Sodium chloride | 5 g |
| Disodium phosphate | 2.5 g |
| Agar - added to final concentrate of 1% (w/v) | |
| Culture medium pH is 6 | |

The plates were then incubated for 24 hours under aerobic conditions at a temperature of 37° C.

Recovery of antibiotic substances

1. Freeze-thaw extraction

This step was carried out according to a modification of the method of McGeachie J., Zentrabl. Bakteriol (Orig A), 196 (1965), p 377–384. The culture was stored overnight at a temperature of −20° C., thereafter thawed at room temperature and the fluid thereby expressed was collected. This expressed fluid was then subjected to centrifugation at 3,000 g for 1 hr at 4° C. The supernatant thus obtained is referred to herein as crude freeze-thaw extract.

1a. Centrifugation

In the alternative case where incubation was effected aerobically for 48 hours at 37° C. in Brain Heart Infusion Broth with the use of an orbital shaker, the incubated broth was centrifuged at 3000 g for 30 minutes to remove cell material. The supernatant thus obtained was subsequently treated in the same manner as described for crude freeze-thaw extract.

2. Ammonium sulphate precipitation

Solid ammonium sulphate (analar, B.D.H.) was added to the crude freeze-thaw extract to provide 30% saturation. After stirring at 4° C. for 3 h, the precipitate thereby obtained (which contained some of the protein present in the extract) was removed by centrifugation at 3,000 g for 1 h at 4° C. Further solid ammonium sulphate was then added to provide 50% saturation. After stirring overnight at 4° C., the precipitate obtained (which contained the antibiotic substances to be recovered) was again separated by centrifugation as described above. This second precipitate was dissolved in the minimum amount of 0.05 M phosphate buffer, pH 6.0 at 4° C. and undissolved precipitate was again removed by centrifugation to provide a supernatant for further purification.

3. Ion-exchange chromatography

A 10 ml sample of the supernatant obtained by ammonium sulphate precipitation was loaded on to a Sephadex C-25 cation exchange column (column dimensions 1.5×30 cm) pre-equilibrated with 0.05 M phosphate buffer, pH 6.0. Unbound substances were eluted with starting buffer at room temperature. Bound substances were thereafter eluted at a flow rate of 15 ml h$^{-1}$ using a linearly increasing ionic strength gradient of 0–0.5 M (400 ml) NaCl in 0.05 M phosphate buffer, pH 6.0 at room temperature. The high molecular weight antibiotic substance was unbound and was obtained in the eluate with starting buffer. During elution, 5.5 ml fractions were collected and those containing the low molecular weight antibiotic (identified by their inhibitory 4. Gel filtration chromatography 10 ml of peak fractions from ion-exchange chromatography containing the low molecular weight antibiotic were loaded on to a Sephadex G25 column (2.2×45 cm, $V_o$=61.5 ml, $V_t$=141 ml) pre-equilibrated with 0.05 M phosphate buffer, pH 6. The column was eluted with 0.05 M phosphate buffer, pH 6.0 at a flow rate of 12 ml h$^{-1}$ at room temperature, and 4 ml fraction some of which contained the low molecular weight antibiotic (again identified by their inhibitory activity against MF 121) were collected.

The following Table 4 summarises the results obtained:

TABLE 4

| Fraction | Total units of inhibitory activity against S. cohnii + | Total protein mg | Specific activity units mg$^{-1}$ protein | Yield, % |
|---|---|---|---|---|
| Crude freeze-thaw extract | 12,800 | 2,560 | 5 | |
| 30–50% ammonium sulphate precipitate | 10,400 | 50.50 | 202.80 | 80 |
| *C25-Unbound high molecular weight antibiotic | 185.80 | | | 1.45 |
| *C25-Bound low molecular weight antibiotic (all fractions) | 5,110.60 | 3.27 | 1,561.40 | 39.90 |
| C-25 bound low molecular weight antibiotic (peak fractions) | 4,659.20 | 1.17 | 3,983.10 | 36.40 |
| **G-25 (all fractions) | 1,194.80 | 0.076 | 15,720.40 | 9.33 |
| **G-25 (peak fractions) | 1,056 | 0.027 | 39,111.10 | 8.25 |

*Sephadex C-25 cation-exchanger
**Sephadex G-25 column
+ S. cohnii - MF 121.

Protein Assay

In the above Table and throughout the specification, protein was estimated by the method of Lowry, O. H., Rosgbrough, N. J., Farr, A. L. and Randall, R. J., J. Biol. Chem., 193 (1951), p 265–275, using bovine serum albumin as reference.

Minimal Nutrition Studies

To further investigate the production of the antibiotic substances of the present invention, minimal nutrition studies have been carried out. In these studies, isolates of the strain S. epidermidis NCIB 11536 (taken from a stock culture maintained in 40% (v/v) glycerol/PBS as described above) were incubated aerobically for 24 hours at 37° C. with the use of an orbital shaker. Incubation took place in a synthetic medium as described above but wherein several components had been replaced, omitted or were at different concentrations. Referring to the synthetic medium described above, for the minimal nutrition studies the phosphate content was reduced to 200 mg l$^{-1}$ Na H$_2$ PO$_4$, PIPES were replaced by 10000 mg l$^{-1}$ MES (2(morpholino) ethanesulphonic acid), K$_2$HPO$_4$ was replaced by 500 mg l$^{-1}$ KCl and the glucose content was set at 2000 mg l$^{-1}$. Taking this synthetic medium as the basis for the minimal nutrition studies, the amino acid contents of the synthetic media were varied by the omission from the media of various amino acids. It was found that the amino acid content of the synthetic medium could be reduced to 800 mg l$^{-1}$ L-arginine, 400 mg $l^{-1}$ L-cysteine,
2000 mg $l^{-1}$ L-glutamic acid,
400 mg $l^{-1}$ glycine,
400 mg $l^{-1}$ L-proline
400 mg $l^{-1}$ L-tryptophan and
400 mg $l^{-1}$ L-histidine
without preventing growth of *S. epidermidis* NCIB 11536 or production of the antibiotic substances of the present invention.

In these studies it was also found that raising the total amino acid concentration from 2800 mg $l^{-1}$ to 11200 mg $l^{-1}$ resulted in an 8- to 16-fold increase in titre whilst bacterial yield rose by only 1%.

These results indicate amino acid composition to have a pronounced effect on antibiotic production.

Ultra-Violet Absorption Spectra

FIGS. 3, 4 and 5 of the accompanying drawings illustrate U.V. spectra recorded in the absorbance range of 200–300 nm with three samples of the low molecular weight antibiotic substance obtained by the aerobic culture of *S. epidermidis* NCIB 11536. The samples each showed an absorption peak centered at about 210 nm and a weaker absorption peak centered about 270–280 nm. FIGS. 3 and 4 illustrate U.V. spectra of samples of the antibiotic substance following ion-exchange chromatography by elution through a Sephadex C-25 cation exchange column and represent titres of 256 and 512 units $ml^{-1}$ respectively. FIG. 5 illustrates the UV spectra of a sample of the antibiotic substance following gel filtration chromatography by elution through a Sephadex G-25 column.

We claim:

1. An antibiotic polypeptide compound produced by *Staphylococcus epidermidis* NCIB 11536 or a mutant strain thereof, or an acid addition salt thereof, having a molecular weight of from about 950 to 10,000 and possessing bactericidal and bacteriolytic properties with respect to Gram-positive bacteria, said compound comprising within its peptide chain one residue of proline, two residues of glycine, and at least one residue of each of the amino acids isoleucine, phenylalanine, alanine, aspartic acid, glutamic acid, and lysine, said compound having UV absorption maxima at about 210 nm and at from about 260 to 280 nm, and said compound having a thermostability, when in a liquid medium, which is enhanced by acidity.

2. The antibiotic polypeptide compound of claim 1 which is produced from *Staphylococcus epidermidis* NCIB 11536.

3. The antibiotic polypeptide compound of claim 1 for use in a method of treatment of the human or animal body to combat Gram-positive bacterial infections.

4. The antibiotic polypeptide compound of claim 3 for use in treatment of acne, impetigo, or infected eczema in humans.

* * * * *